United States Patent
Westergaard et al.

(10) Patent No.: US 11,555,750 B2
(45) Date of Patent: Jan. 17, 2023

(54) FORCE TRANSDUCER, A MEASURING DEVICE AND A SYSTEM FOR MEASURING MUSCLE STIFFNESS

(71) Applicants: Københavns Universitet, Copenhagen (DK); Movotec A/S, Charlottenlund (DK)

(72) Inventors: Johnny Erik Westergaard, Stenløse (DK); Peder Esben Bilde, Frederiksberg (DK); Jens Bo Nielsen, Virum (DK)

(73) Assignees: Københavns Universitet, København K (DK); Movotec A/S, Charlottenlund (DK)

( * ) Notice: Subject to any disclaimer, the term of this patent is extended or adjusted under 35 U.S.C. 154(b) by 254 days.

(21) Appl. No.: 17/051,419

(22) PCT Filed: Apr. 25, 2019

(86) PCT No.: PCT/EP2019/060569
§ 371 (c)(1),
(2) Date: Oct. 28, 2020

(87) PCT Pub. No.: WO2019/211151
PCT Pub. Date: Nov. 7, 2019

(65) Prior Publication Data
US 2021/0231511 A1    Jul. 29, 2021

(30) Foreign Application Priority Data

May 3, 2018    (EP) .................................... 18170570

(51) Int. Cl.
*G01L 1/00*    (2006.01)
*G01L 1/22*    (2006.01)
*A61B 5/22*    (2006.01)

(52) U.S. Cl.
CPC ............ *G01L 1/2218* (2013.01); *A61B 5/225* (2013.01); *G01L 1/2262* (2013.01); *A61B 2562/0261* (2013.01)

(58) Field of Classification Search
CPC ..... G01L 1/2218; G01L 1/2262; A61B 5/225; A61B 2562/0261
See application file for complete search history.

(56) References Cited

U.S. PATENT DOCUMENTS

| | | | |
|---|---|---|---|
| 4,006,629 A * | 2/1977 | Barrett | B25B 23/1425 73/862.26 |
| 4,454,769 A | 6/1984 | Loos | |

(Continued)

FOREIGN PATENT DOCUMENTS

| | | |
|---|---|---|
| GB | 687823 A | 2/1953 |
| GB | 1577341 A | 10/1980 |

(Continued)

*Primary Examiner* — Max H Noori
(74) *Attorney, Agent, or Firm* — Knobbe Martens Olson & Bear, LLP

(57) ABSTRACT

A force transducer is disclosed, which is arranged in such a way that, when a force is applied to the force transducer, two output signals from the force transducer are generated, which output signals are representative of the force components in a first plane and in a second plane perpendicular to the first plane, respectively, whereas force components in a third plane perpendicular to the first plane and the second plane do not affect the output signals from the force transducer. Furthermore, a measuring device is disclosed, comprising a handle comprising such a force transducer and a base unit, to which the handle is attached. Even further, a system for measuring muscle stiffness is disclosed, comprising a measuring unit and a processing unit, the measuring unit comprising such a measuring device.

10 Claims, 8 Drawing Sheets

(56) References Cited

U.S. PATENT DOCUMENTS

Figure 1:
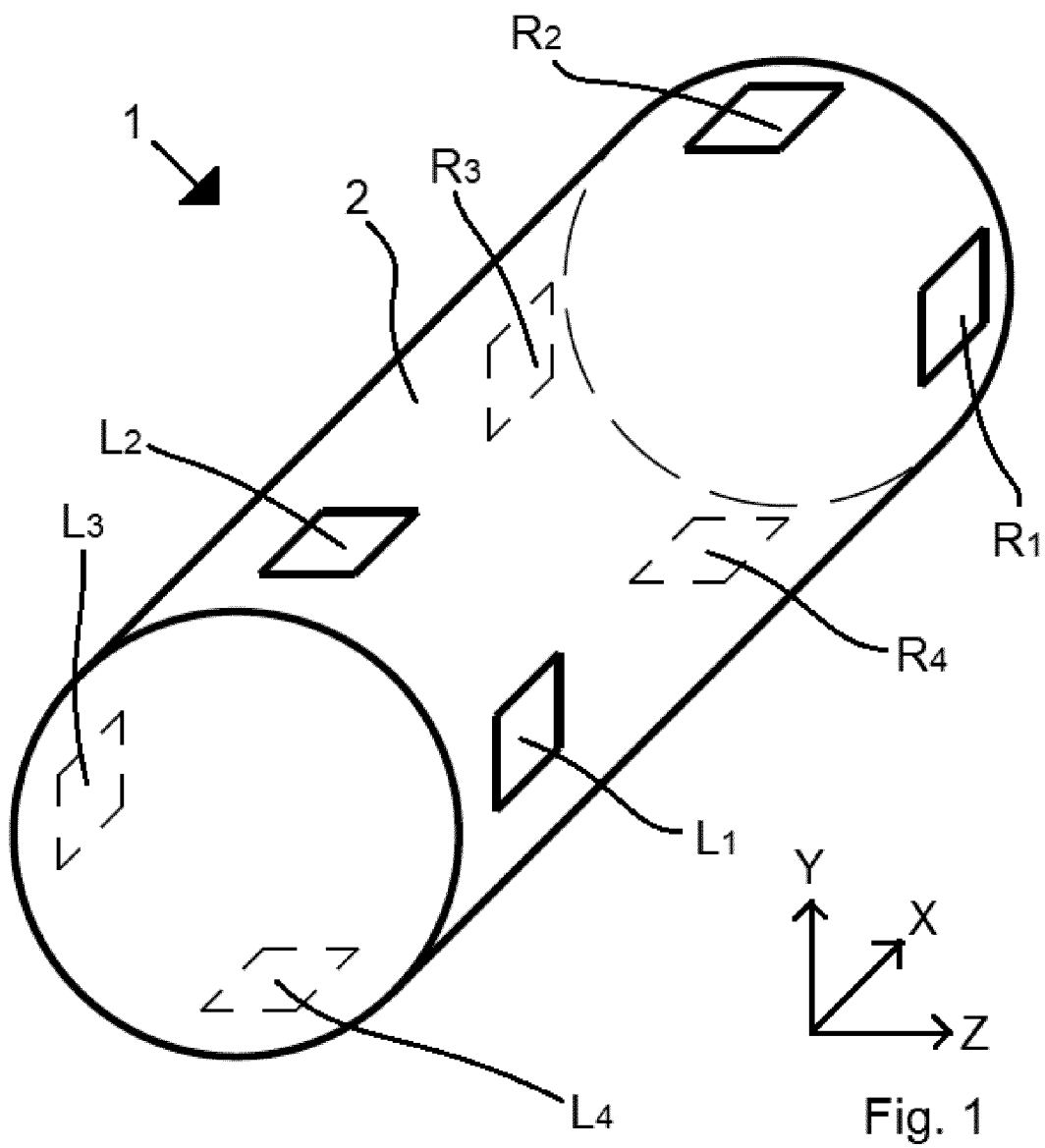

| | | | |
|---|---|---|---|
| 4,697,661 A | 10/1987 | Pajerski | |
| 4,911,024 A | 3/1990 | McMaster | |
| 5,386,724 A | 2/1995 | Das | |
| 5,576,704 A * | 11/1996 | Baker | G05G 9/047 341/20 |
| 5,671,266 A | 9/1997 | Linhart | |
| 5,872,320 A | 2/1999 | Kamentser | |
| 9,134,187 B1 * | 9/2015 | Organ | G05G 5/05 |
| 2001/0032743 A1 * | 10/2001 | Kamen | B60L 15/2036 180/218 |
| 2007/0027631 A1 | 2/2007 | Cabrera | |
| 2013/0068037 A1 | 3/2013 | Siklos | |
| 2013/0121477 A1 * | 5/2013 | Lee | A61B 6/4482 378/197 |
| 2013/0289448 A1 | 10/2013 | Landry | |
| 2014/0245838 A1 | 9/2014 | Nagano | |
| 2015/0160081 A1 | 6/2015 | Carignan | |
| 2016/0317066 A1 | 11/2016 | Wang | |
| 2017/0049363 A1 | 2/2017 | Kim | |
| 2017/0181689 A1 | 6/2017 | Lin | |
| 2017/0245798 A1 * | 8/2017 | Ohkoshi | A61B 5/14532 |
| 2017/0253270 A1 | 12/2017 | Griffiths | |
| 2020/0289890 A1 * | 9/2020 | Kim | G01C 19/00 |
| 2022/0234197 A1 * | 7/2022 | Kobayashi | B25J 9/1664 |

FOREIGN PATENT DOCUMENTS

| | | |
|---|---|---|
| GB | 2093191 A | 8/1982 |
| WO | WO 2014/113456 A1 | 7/2014 |
| WO | WO 2016/001668 A1 | 1/2016 |

\* cited by examiner

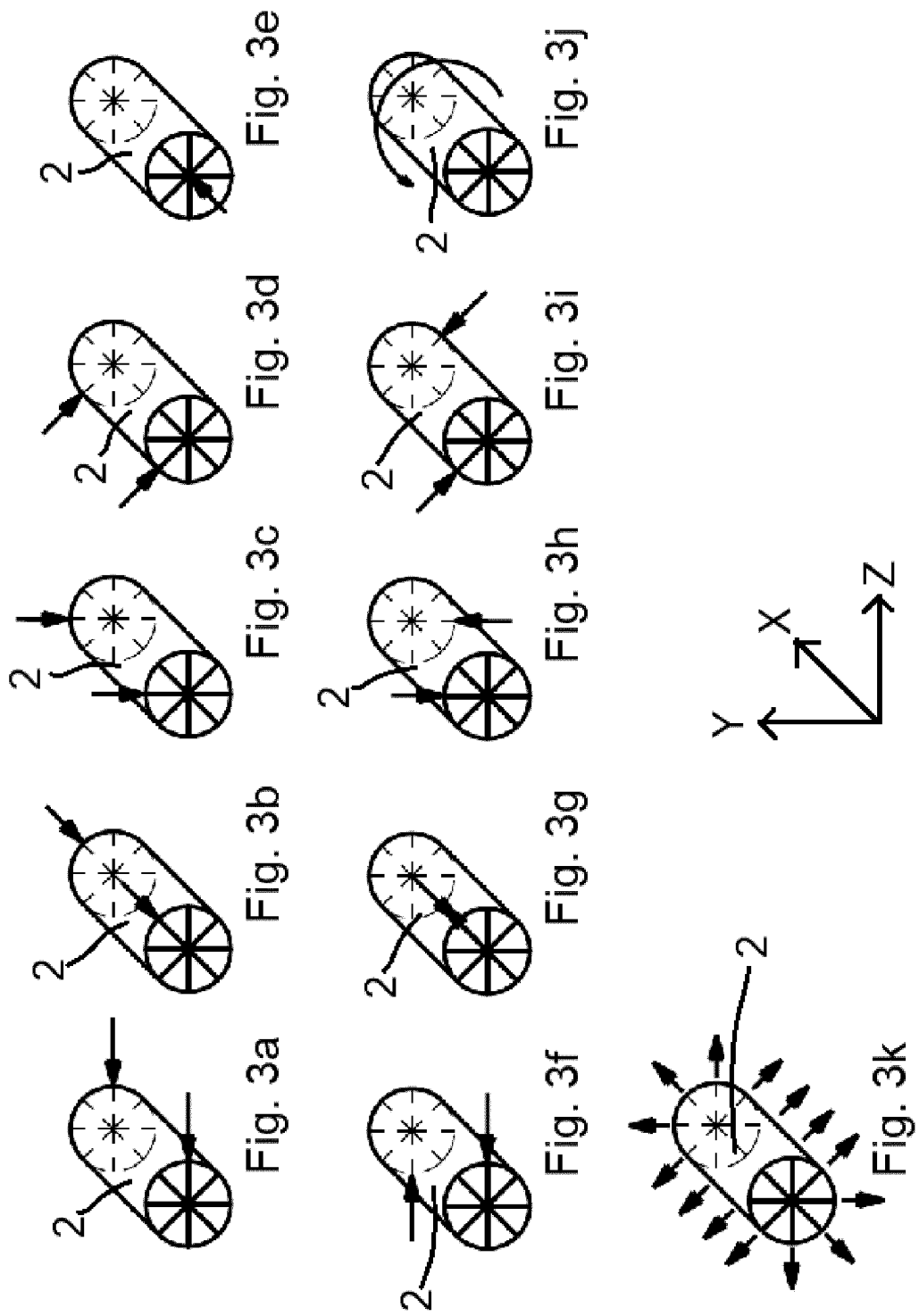

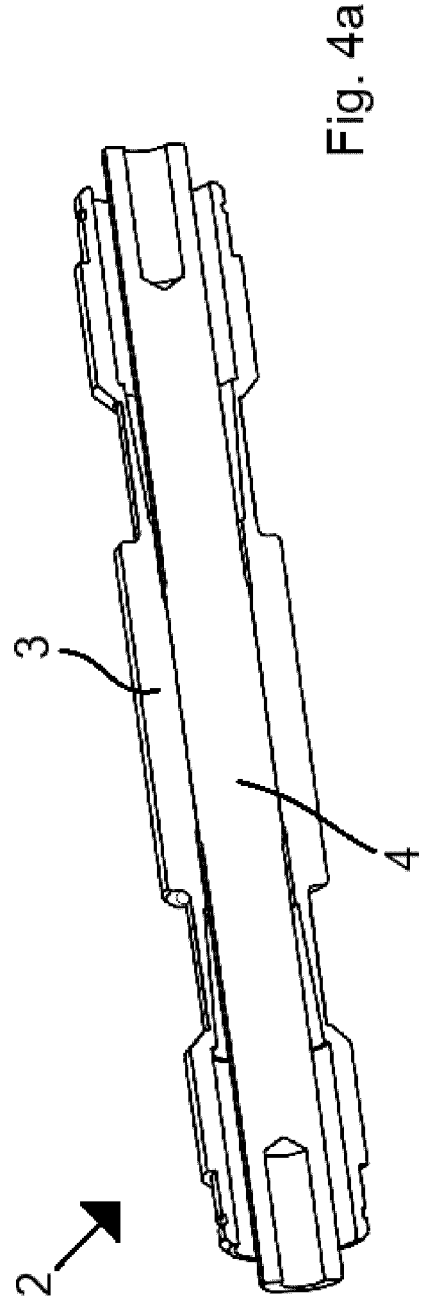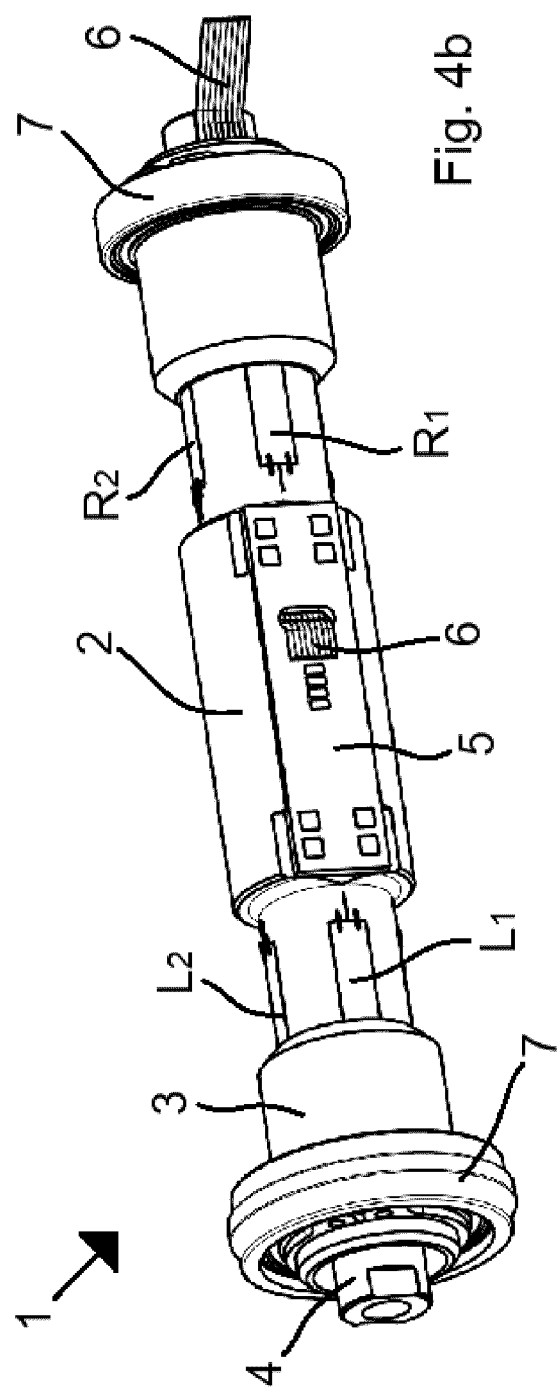

FORCE TRANSDUCER, A MEASURING DEVICE AND A SYSTEM FOR MEASURING MUSCLE STIFFNESS

CROSS REFERENCE TO RELATED APPLICATIONS

This application is a U.S. National Phase Application of PCT International Application Number PCT/EP2019/060569, filed on Apr. 25, 2019, designating the United States of America and published in the English language, which is an International Application of and claims the benefit of priority to European Patent Application No. 18170570.8, filed on May 3, 2018. The disclosures of the above-referenced applications are hereby expressly incorporated by reference in their entireties.

The present invention relates to a force transducer, more particularly to a force transducer, which is able to measure force components in some directions and ignore force components in other directions. Furthermore, the invention relates to a measuring device and a system for measuring muscle stiffness comprising such a force transducer.

BACKGROUND OF THE INVENTION

In some applications, for instance when measuring the force applied to a human body part for obtaining a measure of the muscle stiffness, it is important to measure some direction components of a force relatively precisely, whereas other direction components of the force are not relevant.

Known force transducers, however, are not enable to distinguish sufficiently between the different direction components of the force applied, which means the force components in the irrelevant directions influence the measurements of the force components in the relevant directions. In other words, the irrelevant force components constitute noise signals, which disturb the measurement of the relevant force components.

BRIEF DESCRIPTION OF THE INVENTION

It is an object of the present invention to provide a force transducer without the above-mentioned disadvantages of force transducers known within the art as well as a few applications of such a force transducer.

The present invention relates to a force transducer, which is arranged in such a way that, when a force is applied to the force transducer, two output signals from the force transducer are generated, which output signals are representative of the force components in a first plane and in a second plane perpendicular to the first plane, respectively, whereas force components in a third plane perpendicular to the first plane and the second plane do not affect the output signals from the force transducer.

A force transducer with such a configuration eliminates the above-mentioned disadvantages of known force transducers.

In an embodiment of the invention, the force transducer is further arranged in such a way that no torque applied to the force transducer will affect the output signals from the force transducer.

If the force transducer is configured to ignore torques applied to it, the force measurement is even less likely to be disturbed by noise signals.

In an embodiment of the invention, the force transducer comprises an elongated core part, wherein each of the two output signals are generated by four strain gauges coupled electrically in a bridge coupling and arranged physically on one or more surfaces of the core part with the strain sensitive direction parallel to a longitudinal axis of the core part, wherein two of the four strain gauges of each bridge coupling are arranged near one end of the core part and the other two are arranged near the opposite end of the core part with two of the strain gauges arranged in a common plane on one side of the core part and the other two strain gauges arranged in another common plane parallel thereto on the opposite side of the core part, and wherein the two common planes of the four strain gauges of one bridge coupling are perpendicular to the two common planes of the four strain gauges of the other bridge coupling.

Such a configuration of the force transducer has proven to result in reliable and precise measurements using only relatively few electronic components.

In an embodiment of the invention, for each bridge coupling, the two strain gauges on one side of the core part are arranged to respond positively when stretched and negatively when compressed, and the two strain gauges on the opposite side of the core part are arranged to respond negatively when stretched and positively when compressed.

With such an arrangement of the strain gauges, it is possible to obtain relatively large and uniform output signals corresponding to the relevant direction components of the applied forces and, at the same time, eliminate any influence on the output signals from irrelevant direction component.

In an embodiment of the invention, one or more printed circuit boards are mounted onto the core part, which printed circuit board(s) at least comprise(s) front-end electronics for the two strain gauge bridge couplings.

In an embodiment of the invention, the core part is substantially cylindrical.

In an aspect of the invention, it relates to a measuring device comprising a handle comprising a force transducer as described above, wherein the force transducer is arranged, when a force is applied to the handle, to measure force components in directions perpendicular to a longitudinal axis of the handle and to ignore any force components in a direction parallel to the longitudinal axis of the handle, and a base unit, to which the handle is attached.

In an embodiment of the invention, the outer part of the handle is arranged to be able to rotate freely around the core part, for instance by means of ball bearings arranged around the two ends of the core part, respectively.

Letting the outer part of the handle be able to rotate freely around the core part means that the measuring device is not subjected to any torque applied to the handle around its longitudinal axis.

In an embodiment of the invention, the base unit comprises a connection part for releasably attaching the measuring device to an orthosis for being applied to a body segment of a person.

In an embodiment of the invention, the connection part is of the bayonet joint type so that the measuring unit can be attached to the orthosis by simply inserting one into the other and rotating the two parts relatively to each other, and the two parts can be detached from each other by rotating them relatively to each other in the opposite direction and pulling them apart.

In an embodiment of the invention, the measuring device further comprises, preferably within the base unit, one or more of the following: a microcontroller, a 3-axis accelerometer, a 3-axis gyroscope, a 3-axis magnetometer, analogue front-end electronics for a set of EMG probes, a communication module, for example Bluetooth, a power source, for example a rechargeable battery.

Such configurations of the measuring device make it ideal for being used in a system for measuring muscle stiffness.

In an aspect of the invention, it relates to a system for measuring muscle stiffness in a predetermined joint of an individual, the system comprising a measuring unit and a processing unit, the measuring unit being configured to be applied to a body segment of the predetermined joint and comprising at least one measuring device as described above, and wherein the processing unit is configured to receive a plurality of data sets from the at least one measurement device, analyse the plurality of data sets for one or more indications of an elicited stretch reflex based on the measurement data, and calculate a muscle stiffness score based on the measurement data.

THE DRAWINGS

Figure 2A:
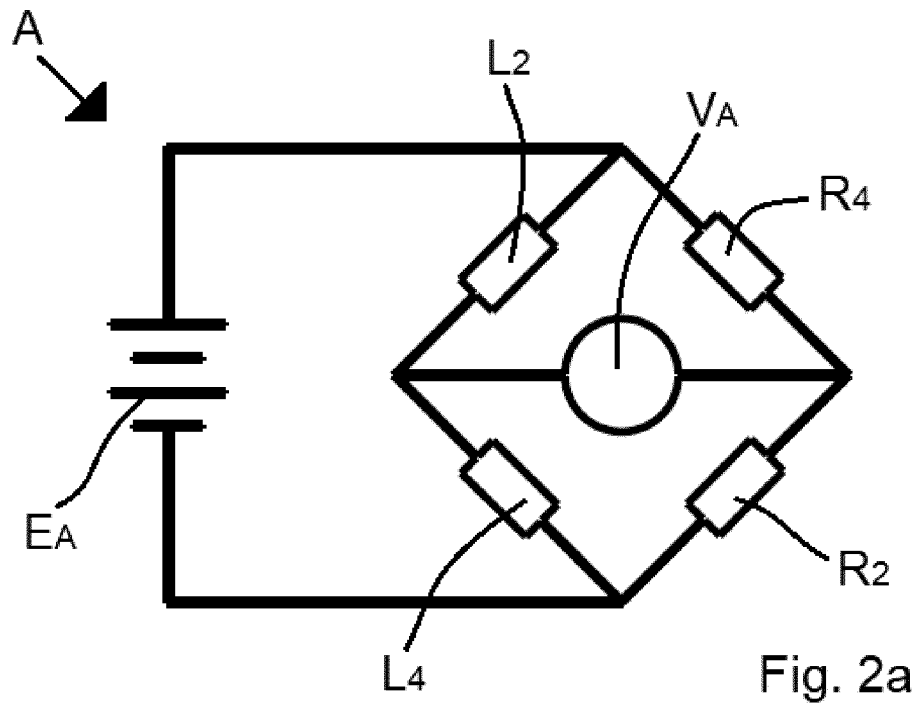
Figure 2B:
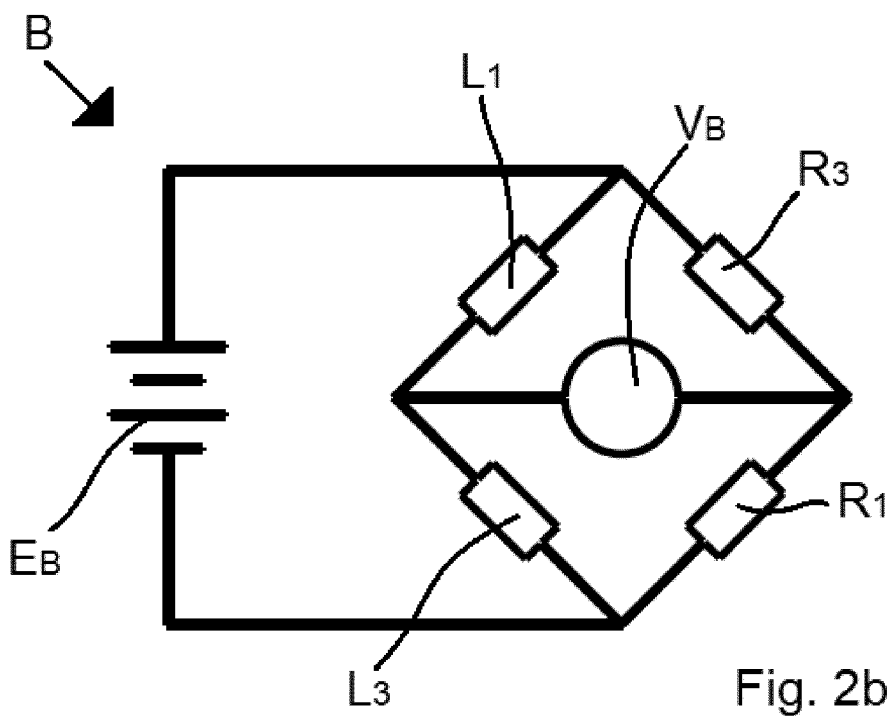
Figure 5A:
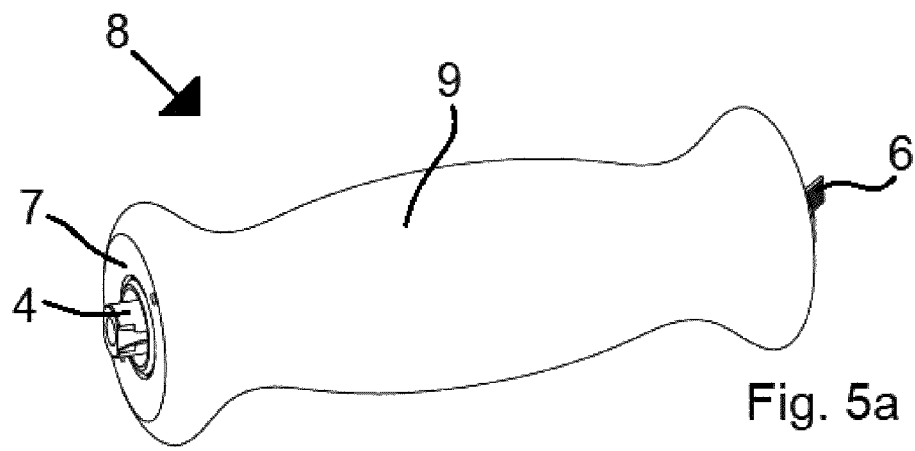
Figure 5B:
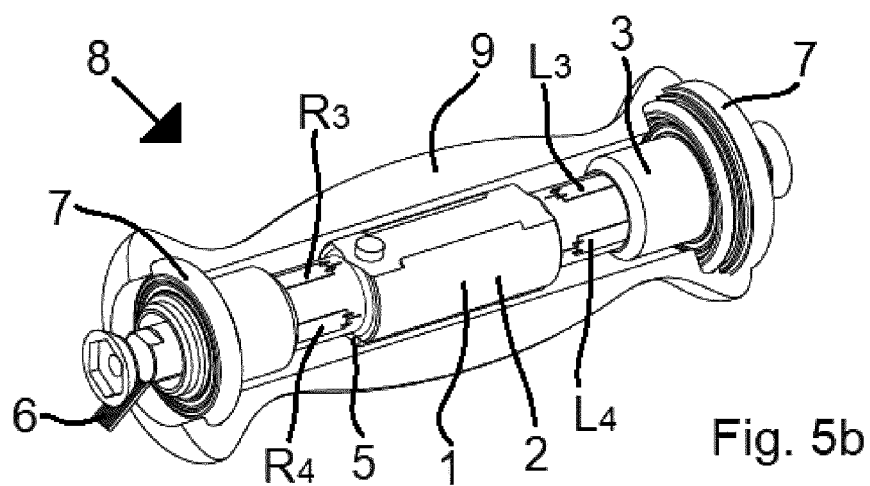
Figure 5C:
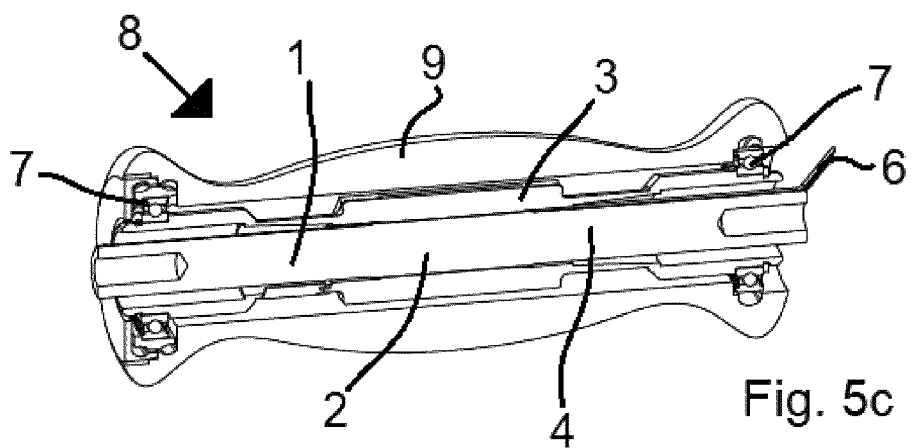
Figure 6A:
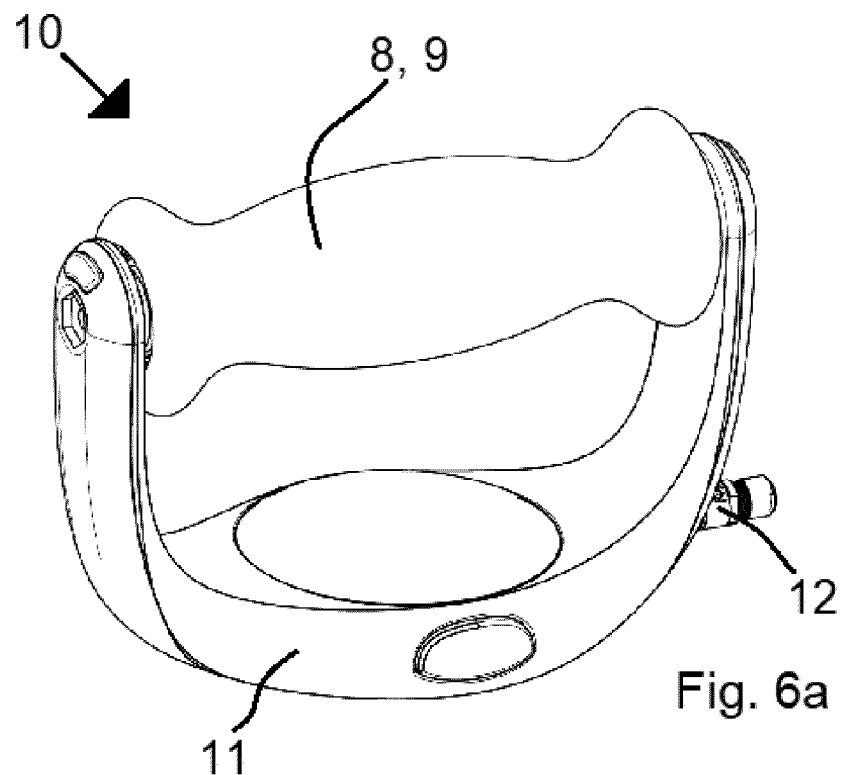
Figure 6B:
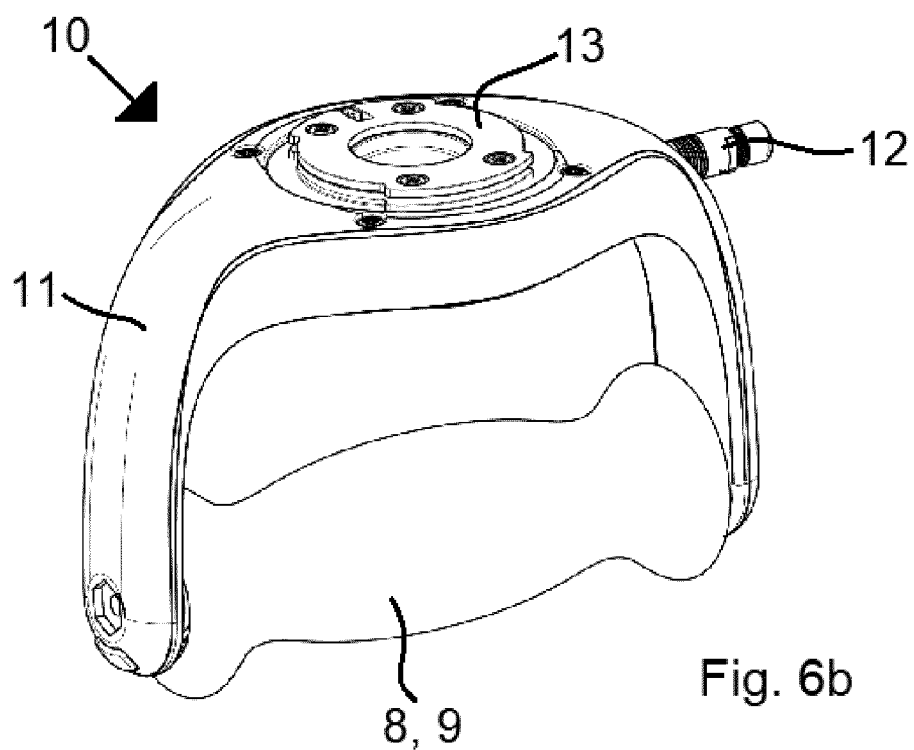
Figure 6C:
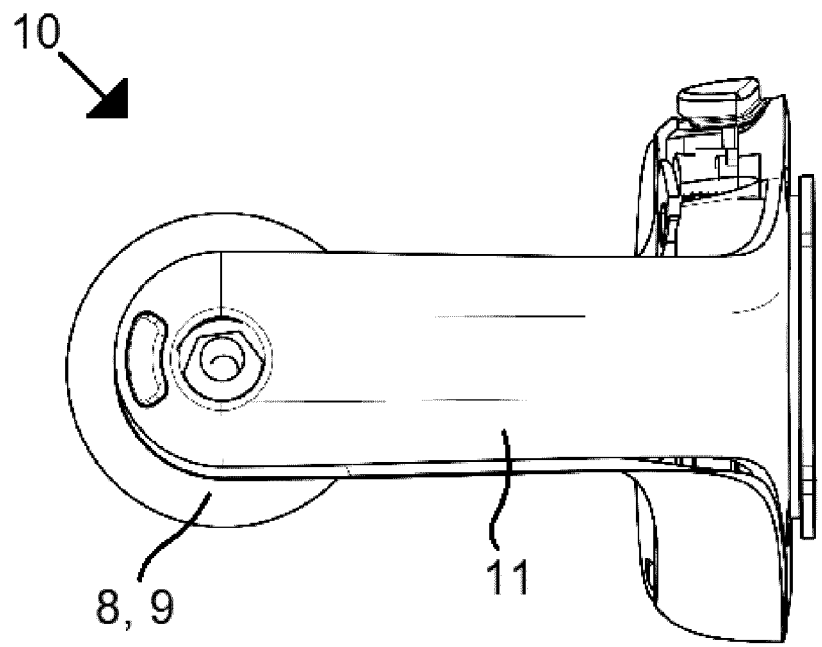
Figure 6D:
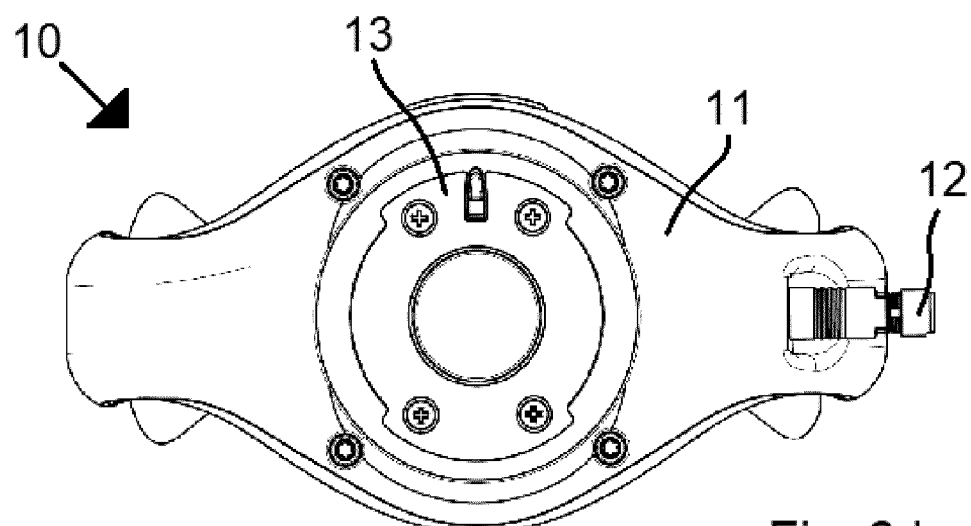
Figure 7:
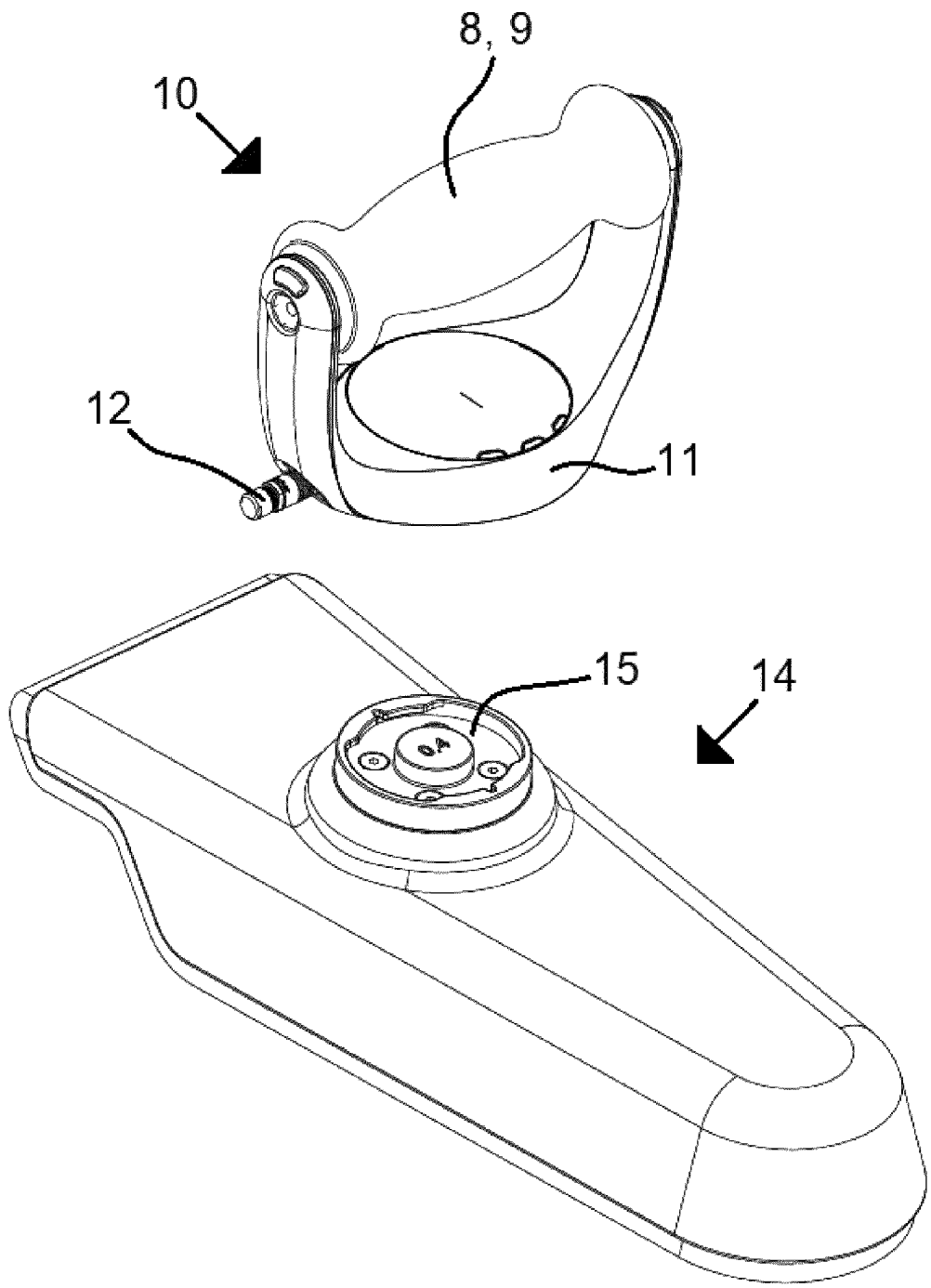

In the following, a few exemplary embodiments of the invention are described in further detail with reference to the drawings, of which FIG. 1 is a schematic illustration of a strain gauge layout of a force transducer according to an embodiment of the invention, FIG. 2a is an electric diagram of a first signal channel of a force transducer according to an embodiment of the invention, FIG. 2b is an electric diagram of a second signal channel of a force transducer according to an embodiment of the invention, FIG. 3a is a schematic illustration of a force applied in a first direction to a core part of a force transducer according to an embodiment of the invention, FIG. 3b is a schematic illustration of a force applied in a second direction to a core part of a force transducer according to an embodiment of the invention, FIG. 3c is a schematic illustration of a force applied in a third direction to a core part of a force transducer according to an embodiment of the invention, FIG. 3d is a schematic illustration of a force applied in a fourth direction to a core part of a force transducer according to an embodiment of the invention, FIG. 3e is a schematic illustration of a force applied in a fifth direction to a core part of a force transducer according to an embodiment of the invention, FIG. 3f is a schematic illustration of a torque applied in a first direction to a core part of a force transducer according to an embodiment of the invention, FIG. 3g is a schematic illustration of a torque applied in a second direction to a core part of a force transducer according to an embodiment of the invention, FIG. 3h is a schematic illustration of a torque applied in a third direction to a core part of a force transducer according to an embodiment of the invention, FIG. 3i is a schematic illustration of a torque applied in a fourth direction to a core part of a force transducer according to an embodiment of the invention, FIG. 3j is a schematic illustration of a torque applied in a fifth direction to a core part of a force transducer according to an embodiment of the invention, FIG. 3k is a schematic illustration of thermal expansion of a force transducer according to an embodiment of the invention, FIG. 4a is a schematic illustration of a core part of a force transducer according to an embodiment of the invention, FIG. 4b is a schematic illustration of a force transducer according to an embodiment of the invention, FIG. 5a is a perspective view of a handle of a measuring device according to an embodiment of the invention, FIG. 5b is a perspective view of the handle shown in FIG. 5a with some parts removed, FIG. 5c is a cross-sectional view of the handle shown in FIG. 5a, FIG. 6a is a perspective view of a measuring device according to an embodiment of the invention seen obliquely from above, FIG. 6b is a perspective view of the measuring device shown in FIG. 6a seen obliquely from below, FIG. 6c is a side view of the measuring device shown in FIG. 6a, FIG. 6d is a bottom view of the measuring device shown in FIG. 6a, and FIG. 7 is a perspective view of a measuring unit of a system for measuring muscle stiffness according to an embodiment of the invention.

DETAILED DESCRIPTION OF THE INVENTION

FIG. 1 is a schematic illustration of a strain gauge layout of a force transducer 1 according to an embodiment of the invention. It illustrates how eight strain gauges $L_1$, $L_2$, $L_3$, $L_4$, $R_1$, $R_2$, $R_3$, $R_4$ are arranged on the outer surface of a cylindrical core part 2.

Four of the strain gauges $L_1$, $L_2$, $L_3$, $L_4$ are arranged around the core part 2 near a first (left) end thereof, whereas the remaining four strain gauges $R_1$, $R_2$, $R_3$, $R_4$ are arranged around the core part 2 near the other (right) end thereof.

Each of the eight strain gauges $L_1$, $L_2$, $L_3$, $L_4$, $R_1$, $R_2$, $R_3$, $R_4$ are arranged opposite one of the other strain gauges $L_3$, $L_4$, $L_1$, $L_2$, $R_3$, $R_4$, $R_1$, $R_2$ and in the same plane as another one of the other strain gauges $R_1$, $R_2$, $R_3$, $R_4$, $L_1$, $L_2$, $L_3$, $L_4$.

Thus, strain gauges $L_1$ and $R_1$ are arranged in a common plane opposite strain gauges $L_3$ and $R_3$, respectively, and strain gauges $L_2$ and $R_2$ are arranged in a common plane opposite strain gauges $L_4$ and $R_4$, respectively. Furthermore, the two parallel planes, in which strain gauges $L_1$, $R_1$, $L_3$ and $R_3$ are arranged, are perpendicular to the two parallel planes, in which strain gauges $L_2$, $R_2$, $L_4$ and $H_4$ are arranged.

Electrically, four of the strain gauges $L_2$, $L_4$, $R_2$, $R_4$ are connected in a first bridge coupling of a first signal channel A and the remaining four strain gauges $L_1$, $L_3$, $R_1$, $R_3$ are connected in a second bridge coupling of a second signal channel B as illustrated in FIGS. 2a and 2b, respectively.

Using the definition of the X, Y and Z directions as indicated in FIG. 1, the four strain gauges $L_2$, $L_4$, $R_2$, $R_4$ related to the first signal channel A are arranged in the X-Y plane, whereas the four strain gauges $L_1$, $L_3$, $R_1$, $R_3$ related to the second signal channel B are arranged in the X-Z plane In each of the two signal channels A; B, a power source $E_A$; $E_B$ supplies a voltage across the bridge coupling, and an output signal $V_A$; $V_B$ depending on the individual electrical resistances of the four strain gauges $L_2$, $L_4$, $R_2$, $R_4$; $L_1$, $L_3$, $R_1$, $R_3$ forming the bridge coupling can be measured for each of the two signal channels A, B as illustrated in FIGS. 2a and 2b.

The two output signals $V_A$, $V_B$ being proportional with the components in the Z and Y directions, respectively, of a force applied to the force transducer 1, a resulting force signal $V_F$ proportional with the magnitude of the force component perpendicular to the X direction can be calculated from the equation:

$$V_F = \sqrt{V_A^2 + V_B^2}$$

It should be noted that if the signal channels A, B are not balanced, a small "Zero current" will flow across the measuring point and a small output signal $V_A$; $V_B$ will be measured, even in the "Zero output" situations. In such cases, the two output signals $V_A$, $V_B$ are, in fact, not directly proportional with but only linearly related to the force components in the Z and Y directions, respectively.

Either this "Zero current" can be removed by means of an adjustable resistor added to one of the branches of the bridge coupling A; B or the "Zero current" can be accepted and taken into account in the processing of the output signals $V_A$, $V_B$ and the force signal $V_F$.

The eight strain gauges $L_1$, $L_2$, $L_3$, $L_4$, $R_1$, $R_2$, $R_3$, $R_4$ are all arranged on the surface of the core part 2 in such a way that they respond to extensions in the X direction, i.e. in the longitudinal direction of the core part 2. Four of them $L_1$, $L_2$, $R_1$, $R_2$ respond positively when stretched, whereas the other four $L_3$, $L_4$, $R_3$, $R_4$ respond negatively when stretched.

As it will be known to a person skilled within the art, the output signal $V_A$; $V_B$ of a bridge coupling with two positively responding strain gauges $L_2$, $R_2$; $L_1$, $R_1$, and two negatively responding strain gauges $L_4$, $R_4$; $L_3$, $R_3$ arranged as illustrated in FIGS. 2a and 2b will be proportional to the sum strains measured by each of the four strain gauges $L_2$, $L_4$, $R_2$, $R_4$; $L_1$, $L_3$, $R_1$, $R_3$ individually. More particularly, if the same strain is experienced by each of the four strain gauges $L_2$, $L_4$, $R_2$, $R_4$; $L_1$, $L_3$, $R_1$, $R_3$ in such a bridge coupling, the output signal $V_A$; $V_B$ is four times the output signal $V_A$; $V_B$ that would be generated from a single strain gauge $L_1$; $L_2$; $L_3$; $L_4$; $R_1$; $R_2$; $R_3$; $R_4$.

In the following, upward pointing arrows (↑) and downward pointing arrows (↓) are used to indicate "positive" and "negative", respectively. When used in relation with a strain gauge reference, e.g. $L_3$↓, the arrow indicates whether the given strain gauge responds positively or negatively to an extension.

The arrows are also used to indicate whether an impact on a strain gauge $L_1$; $L_2$; $L_3$; $L_4$; $R_1$; $R_2$; $R_3$; $R_4$ is positive (extension) or negative (compression) and to indicate whether the response of a strain gauge $L_1$; $L_2$; $L_3$; $L_4$; $R_1$; $R_2$; $R_3$; $R_4$ is positive or negative. The magnitude of the impact or response is indicated by a factor in the form of a number before the arrow, e.g. 1↑. The unit factor 1 indicates the impact or response caused by a force perpendicular to the plane in which the strain gauge $L_1$; $L_2$; $L_3$; $L_4$; $R_1$; $R_2$; $R_3$ $R_4$ is arranged, whereas, for instance, a force applied in a direction angled 45° relative to the plane, in which the strain gauge $L_1$; $L_2$; $L_3$; $L_4$; $R_1$; $R_2$; $R_3$; $R_4$ is arranged, results in a factor of $1/\sqrt{2} \approx 0.71$.

Thus, if for instance a downward force, i.e. a force in the negative Z direction according to FIG. 1, is applied to the left end of the core part 2, one strain gauge $L_2$↑ will be stretched (1↑) and another strain gauge $L_4$↓ will be shortened (1↓). The response from $L_2$↑ will be 1↑ (=↑*1↑) and the response from $L_4$↓ will also be 1↑ (=↓*1↓). The two other strain gauges $L_1$, $L_3$ in that end of the core part 2 will not be affected and, thus, will give no responses because they are both arranged in planes parallel to the direction of the force.

Obviously, similar considerations can be made for the four strain gauges $R_1$, $R_2$, $R_3$, $R_4$ arranged at the other (right) end of the core part 2.

FIGS. 3a-3k schematically illustrates different force and torque impacts on a core part 2 of a force transducer 1, the responses to which will be discussed in the following.

In FIG. 3a, a force is applied to the core part 2 in the negative Z direction, affecting the core part 2 as a whole and, thus, both ends of the core part 2.

Assuming that eight strain gauges $L_1$, $L_2$, $L_3$, $L_4$, $R_1$, $R_2$, $R_3$, $R_4$ are arranged on the surface of the core part 2 and connected in two bridge couplings A, B as described above and illustrated in FIGS. 1, 2a and 2b, the following schedule can be made:

| Channel | A | | | | B | | | |
|---|---|---|---|---|---|---|---|---|
| Strain gauge | $L_2$↑ | $R_4$↓ | $L_4$↓ | $R_2$↑ | $L_1$↑ | $R_3$↓ | $L_3$↓ | $R_1$↑ |
| Impact | 0 | 0 | 0 | 0 | 1↑ | 1↓ | 1↓ | 1↑ |
| Response | 0 | 0 | 0 | 0 | 1↑ | 1↑ | 1↑ | 1↑ |
| Output signal ($V_A$, $V_B$) | 0 | | | | 4↑ | | | |
| Force signal ($V_F$) | 4 | | | | | | | |

In FIG. 3b, a similar force is applied to the core part 2, only in a direction turned 45° so that it is partly in the negative Z direction and partly in the negative Y direction.

In this case, the schedule looks as follows:

| Channel | A | | | | B | | | |
|---|---|---|---|---|---|---|---|---|
| Strain gauge | $L_2$↑ | $R_4$↓ | $L_4$↓ | $R_2$↑ | $L_1$↑ | $R_3$↓ | $L_3$↓ | $R_1$↑ |
| Impact | 0.71↑ | 0.71↓ | 0.71↓ | 0.71↑ | 0.71↑ | 0.71↓ | 0.71↓ | 0.71↑ |
| Response | 0.71↑ | 0.71↑ | 0.71↑ | 0.71↑ | 0.71↑ | 0.71↑ | 0.71↑ | 0.71↑ |
| Output signal ($V_A$, $V_B$) | 2.83↑ | | | | 2.83↑ | | | |
| Force signal ($V_F$) | 4 | | | | | | | |

In FIG. 3c, the direction of the force has been turned another 45° so that now it is only in the negative Y direction, and the schedule changes accordingly:

| Channel | A | | | | B | | | |
|---|---|---|---|---|---|---|---|---|
| Strain gauge | $L_2$↑ | $R_4$↓ | $L_4$↓ | $R_2$↑ | $L_1$↑ | $R_3$↓ | $L_3$↓ | $R_1$↑ |
| Impact | 1↑ | 1↓ | 1↓ | 1↑ | 0 | 0 | 0 | 0 |
| Response | 1↑ | 1↑ | 1↑ | 1↑ | 0 | 0 | 0 | 0 |
| Output signal ($V_A$, $V_B$) | 4↑ | | | | 0 | | | |
| Force signal ($V_F$) | 4 | | | | | | | |

After yet another 45° turn of the direction of the force, the situation in FIG. 3d is reached, in which the direction of the force is partly in the positive Z direction and partly in the negative Y direction, resulting in the following schedule:

| Channel | A | | | | B | | | |
|---|---|---|---|---|---|---|---|---|
| Strain gauge | $L_2$↑ | $R_4$↓ | $L_4$↓ | $R_2$↑ | $L_1$↑ | $R_3$↓ | $L_3$↓ | $R_1$↑ |
| Impact | 0.71↑ | 0.71↓ | 0.71↓ | 0.71↑ | 0.71↓ | 0.71↑ | 0.71↑ | 0.71↓ |
| Response | 0.71↑ | 0.71↑ | 0.71↑ | 0.71↑ | 0.71↓ | 0.71↓ | 0.71↓ | 0.71↓ |
| Output signal ($V_A$, $V_B$) | 2.83↑ | | | | 2.83↓ | | | |
| Force signal ($V_F$) | 4 | | | | | | | |

Thus, in the situations illustrated in FIGS. 3a-3d, in which the forces are all perpendicular to the X direction, i.e. in the plane, in which the force transducer 1 is intended to measure the force, the magnitude of the force signal is the same in all directions and the sensitivity of the system is high, which is indicated by the magnitude 4 of the force signal $V_F$.

In FIG. 3e, the situation is different. Now, the force is applied to the core part 2 in the positive X direction. This results in the following schedule:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | $1\uparrow$ | 0 | $1\uparrow$ | 0 | $1\uparrow$ | 0 | $1\uparrow$ | 0 |
| Response        | $1\uparrow$ | 0 | $1\downarrow$ | 0 | $1\uparrow$ | 0 | $1\downarrow$ | 0 |
| Output signal ($V_A$, $V_B$) | | | 0 | | | | 0 | |
| Force signal ($V_F$) | | | | | 0 | | | |

Thus, as desired, the system is insensitive to force components in the X direction.

Turning now to torques rather than forces applied to the core part 2, FIGS. 3f-3i illustrates torques around the Y and Z directions as well as two combinations thereof. For these four situations, the schedules get the following contents:

FIG. 3f:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | 0 | 0 | 0 | 0 | $1\uparrow$ | $1\uparrow$ | $1\downarrow$ | $1\downarrow$ |
| Response        | 0 | 0 | 0 | 0 | $1\uparrow$ | $1\downarrow$ | $1\uparrow$ | $1\downarrow$ |
| Output signal ($V_A$, $V_B$) | | | 0 | | | | 0 | |
| Force signal ($V_F$) | | | | | 0 | | | |

FIG. 3g:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | $0.71\uparrow$ | $0.71\uparrow$ | $0.71\downarrow$ | $0.71\downarrow$ | $0.71\uparrow$ | $0.71\uparrow$ | $0.71\downarrow$ | $0.71\downarrow$ |
| Response        | $0.71\uparrow$ | $0.71\downarrow$ | $0.71\uparrow$ | $0.71\downarrow$ | $0.71\uparrow$ | $0.71\downarrow$ | $0.71\uparrow$ | $0.71\downarrow$ |
| Output signal ($V_A$, $V_B$) | | | 0 | | | | 0 | |
| Force signal ($V_F$) | | | | | 0 | | | |

FIG. 3h:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | $1\uparrow$ | $1\uparrow$ | $1\downarrow$ | $1\downarrow$ | 0 | 0 | 0 | 0 |
| Response        | $1\uparrow$ | $1\downarrow$ | $1\uparrow$ | $1\downarrow$ | 0 | 0 | 0 | 0 |
| Output signal ($V_A$, $V_B$) | | | 0 | | | | 0 | |
| Force signal ($V_F$) | | | | | 0 | | | |

FIG. 3i:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | $0.71\uparrow$ | $0.71\uparrow$ | $0.71\downarrow$ | $0.71\downarrow$ | $0.71\downarrow$ | $0.71\downarrow$ | $0.71\uparrow$ | $0.71\uparrow$ |
| Response        | $0.71\uparrow$ | $0.71\downarrow$ | $0.71\uparrow$ | $0.71\downarrow$ | $0.71\downarrow$ | $0.71\uparrow$ | $0.71\downarrow$ | $0.71\uparrow$ |
| Output signal ($V_A$, $V_B$) | | | 0 | | | | 0 | |
| Force signal ($V_F$) | | | | | 0 | | | |

If the torque is around the X direction, the situation is like illustrated in FIG. 3j. In this case, there is no strain in the X-direction at all, and the schedule becomes very simple:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | 0 | 0 | 0 | 0 | 0 | 0 | 0 | 0 |
| Response        | 0 | 0 | 0 | 0 | 0 | 0 | 0 | 0 |
| Output signal ($V_A$, $V_B$) | | | 0 | | | | 0 | |
| Force signal ($V_F$) | | | | | 0 | | | |

Thus, the system is insensitive to torques in all directions.

Finally, FIG. 3k illustrates a situation of thermal expansion illustrated by outward forces in all directions working on the core part 2. In such a case, the schedule looks like this:

| Channel         | A          |            |            |            | B          |            |            |            |
|-----------------|------------|------------|------------|------------|------------|------------|------------|------------|
| Strain gauge    | $L_2\uparrow$ | $R_4\downarrow$ | $L_4\downarrow$ | $R_2\uparrow$ | $L_1\uparrow$ | $R_3\downarrow$ | $L_3\downarrow$ | $R_1\uparrow$ |
| Impact          | $1\uparrow$ | $1\uparrow$ | $1\uparrow$ | $1\uparrow$ | $1\uparrow$ | $1\uparrow$ | $1\uparrow$ | $1\uparrow$ |
| Response        | $1\uparrow$ | $1\downarrow$ | $1\downarrow$ | $1\uparrow$ | $1\uparrow$ | $1\downarrow$ | $1\downarrow$ | $1\uparrow$ |
| Output signal ($V_A$, $V_B$) | | | 0 | | | | 0 | |
| Force signal ($V_F$) | | | | | 0 | | | |

Thus, the system is also insensitive to thermal expansion.

Summing up on the 11 situations illustrated in FIGS. 3a-3k, the overall conclusion is, that the described system is highly sensitive to force components in the Y and Z directions (which are the force components intended to be measured, i.e. the signal) and insensitive to force components in the X direction as well as torque in all directions and thermal expansion (none of which are desired to have any influence on the measurement, i.e. noise).

FIG. 4a illustrates how the core part 2 can be implemented as two concentric shafts 3, 4 wherein an outer measuring shaft 3 is arranged around an inner shaft 4. In the illustrated embodiment, the measuring shaft 3 is in close connection to and fixed to the inner shaft 4 at the central part of the two shafts 3, 4, whereas, near the ends of the shafts 3, 4, there is a gap between the inner shaft 4 and the measuring shaft 3. This gap ensures that the measuring shaft 3, onto which the strain gauges $L_1$, $L_2$, $L_3$, $L_4$, $R_1$, $R_2$, $R_3$, $R_4$ (not shown in this figure) are mounted, can be bent even when the inner shaft 4 is kept in a fixed position.

FIG. 4b illustrates a force transducer 1 comprising a core part 2 like the one shown in FIG. 4a. Four strain gauges $L_1$, $L_2$, $R_1$, $R_2$ are visible in the figure, whereas the other four $L_3$, $L_4$, $R_3$, $R_4$ are not visible. A printed circuit board 5 comprising the front-end electronics for the two strain gauge bridge couplings A, B is mounted at the central part of the measuring shaft 3 and is connected to the remaining part of the system, in which the force transducer 1 is used, via a cable connection 6. Furthermore, a ball bearing 7 is mounted around each end of the core part 2, so that the core part 2 can rotate freely within the system unit, in which it is arranged.

FIG. 5a illustrates a handle 8 of measuring device 10, in which handle 8 is incorporated a force transducer 1 like the one shown in FIG. 4c. In FIG. 5b, half of the outer part 9 of the handle 8 has been removed so that it is possible to see how the force transducer 1 is arranged within the handle 8. It should be noticed that the handle 8 shown in FIG. 5b is rotated 180° compared to the handle 8 shown in the other figures.

FIG. 5c is a cross-sectional view of the handle 8 shown in FIG. 5a. This figure illustrates how the ball bearings 7 enables the outer part 9 of the handle 8 to rotate freely around the core part 2 of the force transducer 1. This means that no torque around the X direction is transferred to the force transducer 1 from the outer part 9 of the handle 8 when the handle 9 is rotated around its longitudinal axis.

FIGS. 6a and 6b are perspective views of a measuring device 10 of a system for measuring muscle stiffness seen obliquely from above and below, respectively.

Apart from a handle 8 like the one shown in FIGS. 5a-5c, the measuring device 10 comprises a base unit 11 to which the handle 8 is attached. Inside the base unit 11 may be arranged several electronic parts (not shown), such as a microcontroller, a 3-axis accelerometer, a 3-axis gyroscope, a 3-axis magnetometer, analogue front-end electronics for a set of EMG probes, a communication module, for example Bluetooth, and a power source, for example a rechargeable battery.

The measuring device 10 is equipped with an electrical connection 12 for connecting the electronics within the measuring device 10 to a processing unit (not shown) of the system for measuring muscle stiffness (not shown) and with a first mechanical connection part 13 for attaching the measuring device 10 to an orthosis 14 (not shown in these figures). In the illustrated embodiment, the first mechanical connection part 13 is of the bayonet joint type so that the measuring device 10 can be attached to the orthosis by simply inserting the first mechanical connection part 13 into a second mechanical connection part 15 (not shown in these figures) of the orthosis 14 and rotating the two parts relatively to each other.

FIGS. 6c and 6d are a side view and a bottom view, respectively, of the measuring device shown in FIGS. 6a and 6b.

FIG. 7 is a perspective view of a measuring unit of a system for measuring muscle stiffness comprising a measuring device 10 as the one described above and an orthosis 14 with a second mechanical connection part 15 into which the first mechanical connection part 13 of the measuring device 10 is arranged to fit.

When coupled together, the measuring device 10 and the orthosis 14 form a measuring unit, which can be applied to a body segment of a joint of an individual, in which joint the muscle stiffness is to be measured. If the joint is then worked by moving the handle 8 forth and back, the force transducer 1 inside the handle 8 can be used to determine the components of the force applied to the handle 8, which are perpendicular to the longitudinal axis thereof. The ball bearings 7 within the handle 8 ensures that the orthosis 14 and, thereby, the body segment onto which the orthosis 14 is applied are not subjected to any torque applied to the handle 8 around the longitudinal axis thereof.

The output signals $V_A$, $V_B$ and/or the force signal $V_F$ can then be sent to a processing unit (not shown) of the system via the electrical connection 12 together with data from the other electronic parts within the measuring device 10, and the processing unit can analyse the data and calculate a muscle stiffness score based on this analysis. In particular, the data can be sent to the processing units as a plurality of data sets, from which the processing unit can extract possible indications of an elicited stretch reflex, which is useful for determining a muscle stiffness score according to methods known within the art.

LIST OF REFERENCES

1. Force transducer
2. Core part
3. Measuring shaft
4. Inner shaft
5. Printed circuit board
6. Cable connection
7. Ball bearing
8. Handle
9. Outer part of handle
10. Measuring device
11. Base unit
12. Electrical connection to processing unit
13. First mechanical connection part
14. Orthosis
15. Second mechanical connection part
A. First signal channel
B. Second signal channel
$E_A$. Power source for first signal channel
$E_B$. Power source for second signal channel
$L_1$. First strain gauge, Channel B
$L_2$. First strain gauge, Channel A
$L_3$. Second strain gauge, Channel B
$L_4$. Second strain gauge, Channel A
$R_1$. Third strain gauge, Channel B
$R_2$. Third strain gauge, Channel A
$R_3$. Fourth strain gauge, Channel B
$R_4$. Fourth strain gauge, Channel A
$V_A$. Output signal of first signal channel
$V_B$. Output signal of second signal channel

The invention claimed is:

1. A measuring device comprising:
   a force transducer, the force transducer being arranged such that, when a force is applied to the force transducer, two output signals from the force transducer are generated, wherein the output signals are representative of force components in a first plane and in a second plane perpendicular to the first plane, respectively, wherein force components in a third plane perpendicular to the first plane and the second plane do not affect the output signals from the force transducer,
   a handle comprising the force transducer, wherein the force transducer is arranged, when a force is applied to the handle, to measure force components in directions perpendicular to a longitudinal axis of the handle and to ignore any force components in a direction parallel to the longitudinal axis of the handle, and
   a base unit, to which the handle is attached,
   wherein the force transducer comprises an elongated core part and wherein an outer part of the handle is arranged to be able to rotate freely around the core part via ball bearings arranged around two ends of the core part, respectively.

2. The measuring device according to claim 1, wherein the force transducer is further arranged such that no torque applied to the force transducer will affect the output signals from the force transducer.

3. The measuring device according to claim 1,
   wherein each of the two output signals are generated by four strain gauges coupled electrically in a bridge coupling and arranged physically on one or more surfaces of the core part with a strain sensitive direction parallel to a longitudinal axis of the core part,
   wherein two of the four strain gauges of each bridge coupling are arranged near one end of the core part and the other two of the four strain gauges are arranged near the opposite end of the core part, wherein two of the strain gauges are arranged in a common plane on one side of the core part and the other two strain gauges are arranged in another common plane parallel thereto on the opposite side of the core part, and wherein the two common planes of the four strain gauges of one bridge coupling are perpendicular to the two common planes of the four strain gauges of the other bridge coupling.

4. The measuring device according to claim 3, wherein, for each bridge coupling, the two strain gauges on one side of the core part are arranged to respond positively when stretched and negatively when compressed, and the two strain gauges on the opposite side of the core part are arranged to respond negatively when stretched and positively when compressed.

5. The measuring device according to claim 3, wherein one or more printed circuit boards are mounted onto the core part, wherein the printed circuit board(s) at least comprise(s) front-end electronics for the two strain gauge bridge couplings.

6. The measuring device according claim 3, wherein the core part is substantially cylindrical.

7. The measuring device according to claim 1, wherein the base unit comprises a connection part for releasably attaching the measuring device to an orthosis for application to a body segment of a person.

8. The measuring device according to claim 7, wherein the connection part is of a bayonet joint type so that the measuring unit can be attached to the orthosis by inserting one into the other and rotating the two parts relative to each other in one direction, and the two parts can be detached from each other by rotating them relative to each other in an opposite direction and pulling them apart.

9. The measuring device according to claim 1, further comprising, within the base unit, one or more of the following:
- a microcontroller,
- a 3-axis accelerometer,
- a 3-axis gyroscope,
- a 3-axis magnetometer,
- analogue front-end electronics for a set of EMG probes,
- a communication module,
- a power source, for example a rechargeable battery.

10. A system for measuring muscle stiffness in a predetermined joint of an individual, the system comprising a measuring unit and a processing unit, the measuring unit being configured to be applied to a body segment of the predetermined joint and comprising at least one measuring device according to claim 1, and wherein the processing unit is configured to:
- receive a plurality of data sets from the at least one measuring device,
- analyze the plurality of data sets for one or more indications of an elicited stretch reflex based on measurement data from the plurality of data sets;
- calculate a muscle stiffness score based on the measurement data.

* * * * *